(12) United States Patent
Smith

(10) Patent No.: US 7,303,567 B1
(45) Date of Patent: Dec. 4, 2007

(54) CIRCUMCISION DEVICE

(76) Inventor: D. Preston Smith, 616 Scotswood Cir., Knoxville, TN (US) 37919

( * ) Notice: Subject to any disclaimer, the term of this patent is extended or adjusted under 35 U.S.C. 154(b) by 719 days.

(21) Appl. No.: 10/861,844

(22) Filed: Jun. 4, 2004

(51) Int. Cl.
*A61B 17/32* (2006.01)

(52) U.S. Cl. .................................................. 606/118

(58) Field of Classification Search ............... 606/45, 606/118, 167, 174
See application file for complete search history.

(56) References Cited

U.S. PATENT DOCUMENTS

| | | | |
|---|---|---|---|
| 1,417,142 A | | 5/1922 | Couch .................. 606/118 |
| 2,238,660 A | | 4/1941 | Santora ................ 606/118 |
| 2,272,072 A | * | 2/1942 | Ross .................... 606/118 |
| 2,296,594 A | | 9/1942 | Blais et al. ........... 606/118 |
| 2,646,046 A | | 7/1953 | Maryan ................ 606/118 |
| 3,056,407 A | * | 10/1962 | Kariher et al. ....... 606/118 |
| 3,625,218 A | | 12/1971 | Valinoti, Jr. .......... 606/45 |
| 3,793,726 A | | 2/1974 | Schrank ................ 30/151 |
| 3,802,439 A | | 4/1974 | Baumgarten .......... 606/118 |
| 3,893,455 A | * | 7/1975 | McNally ................ 600/41 |
| 5,797,921 A | | 8/1998 | Cimini et al. ........ 606/118 |
| 2007/0060928 A1 | * | 3/2007 | Dave et al. ........... 606/118 |

* cited by examiner

*Primary Examiner*—Vy Q. Bui
(74) *Attorney, Agent, or Firm*—William R. Sharp

(57) ABSTRACT

A circumcision device is provided which comprises: a ring having a tapered interior surface, an open anterior end, an anterior opening defined by the interior surface at the anterior end, an open posterior end, a posterior opening defined by the interior surface at the posterior end which is larger than the anterior opening, a longitudinal axis extending between and through the anterior and posterior openings, an exterior surface, and a groove circumferentially defined around the exterior surface adjacent to the anterior end; a bridge extending over the anterior opening and fixedly connected to the anterior end at circumferentially spaced points thereof; and a handle fixedly but frangibly connected to the bridge at a junction between the handle and bridge, the handle extending longitudinally and outwardly from the junction and being structurally weaker at and adjacent to the junction than any other portion of the handle to thereby make the handle readily breakable and detachable from the bridge at the junction. After the circumcision device is properly positioned and prepared for circumcision of a penis, the bridge (remaining connected to the ring) acts as an obstruction to the glans of the penis to thereby prevent excessive protrusion thereof from the anterior end of the ring, consequently avoiding various complications associated with excessive protrusion of the glans.

11 Claims, 1 Drawing Sheet

CIRCUMCISION DEVICE

BACKGROUND OF THE INVENTION

The invention relates to a particular type of circumcision device designed to avoid complications associated therewith.

Circumcisions have been performed for many years using a circumcision device of the type having a tapered, bell-shaped ring adapted to fit over the glans of a penis and under the foreskin. The ring has an anterior end and a posterior end which is larger than the anterior end. A handle, integral with a bridge as connected to the anterior end, is grasped by the surgeon in properly positioning the ring over the glans. A string or ligature is subsequently tied around the foreskin so as to compress the foreskin into a groove that circumferentially extends around the exterior of the ring. The handle and bridge are then broken off and detached from the ring by means of a structurally weakened junction between the bridge and anterior end of the ring. After about 3-8 days, foreskin under and distal to the ligature dies, and the ring falls off the penis to complete the circumcision.

In some cases, after the circumcision device is positioned and prepared for circumcision with the ring received over the glans, factors such as body movement, penile erection, tissue changes, or simply a missized ring can cause the glans to slip partially or even entirely through the ring and its smaller anterior end so as to excessively protrude therefrom and cause the ring to constrict the penis. As a result, the penis swells and the ring may not fall off the penis after the normal period as intended. In addition to possible infection or damage to the urethra, failure of the ring to fall off the penis necessitates manual removal of the ring, which can require cutting the ring off the penis in an undesirable and delicate procedure.

SUMMARY OF THE INVENTION

It is, therefore, an object of the invention to provide a circumcision device, of the type having a ring, bridge, and handle, which prevents excessive protrusion of the glans from the ring that can lead to the complications described above.

The above object is realized by a circumcision device comprising: a ring having a tapered interior surface, an open anterior end, an anterior opening defined by the interior surface at the anterior end, an open posterior end, a posterior opening defined by the interior surface at the posterior end which is larger than the anterior opening, a longitudinal axis extending between and through the anterior and posterior openings, an exterior surface, and a groove circumferentially defined around the exterior surface adjacent to the anterior end; a bridge extending over the anterior opening and fixedly connected to the anterior end at circumferentially spaced points thereof; and a handle fixedly but frangibly connected to the bridge at a junction between the handle and bridge, the handle extending longitudinally and outwardly from the junction and being structurally weaker at and adjacent to the junction than any other portion of the handle to thereby make the handle readily breakable and detachable from the bridge at the junction.

In performing a circumcision, the ring is adapted to fit over the conically shaped glans of a penis. The groove in the ring is for receiving foreskin as compressed therein by a ligature. The handle can be grasped to manipulate and position the ring. Unlike conventional circumcision devices, however, the handle is detachable from the bridge, which remains connected to the anterior end of the ring. The bridge can then act as an obstruction to the glans of the penis to thereby limit protrusion of the glans from the anterior end of the ring. Complications associated with excessive protrusion of the glans are accordingly avoided by the invention. The preferred longitudinal distance between the anterior opening and the bridge, and thus maximum glans protrusion, is discussed further below.

DETAILED DESCRIPTION OF THE INVENTION

Figure 1:
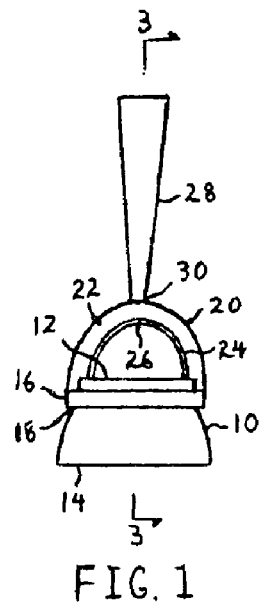
FIG. 1 is an elevational view of one embodiment of the circumcision device in accordance with the invention.

Referring to FIG. 1, the illustrated circumcision device includes a ring 10 having an anterior end 12 and a posterior end 14. An exterior flange 16 is integral with the ring. A junction of flange 16 with ring 10 forms a groove 18 circumferentially defined around the exterior surface of the ring adjacent to anterior end 12.

A bridge 20 is fixedly connected to and preferably integral with anterior end 12 at circumferentially spaced points thereof, which are substantially diametrically opposite one another in the illustrated embodiment. Bridge 20 includes a central bridge portion 22 and a pair of transversely opposing side bridge portions 24, of which only one side bridge portion is visible in FIG. 1. Central bridge portion 22 and side bridge portions 24 are fixedly connected to anterior end 12, and only central bridge portion 22 is fixedly connected to and preferably integral with flange 16. Fixedly connecting central bridge portion 22 to both anterior end 12 and flange 16 makes for a thicker and sturdier connection. Central bridge portion 22 defines with side bridge portions 24 the inner surface 26 of bridge 20. Inner surface 26, extending between the points of connection to anterior end 12, is preferably transversely arcuate (i.e. rounded) in shape. This shape minimizes trauma to the generally conical glans when it, and in particular its rounded tip, comes into contact with inner surface 26.

A handle 28 is fixedly but frangibly (as discussed further below) connected to central bridge portion 22 of bridge 20 at a junction 30 between the handle and bridge.

Figure 2:
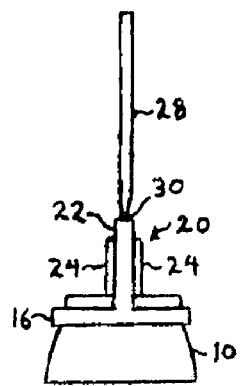
FIG. 2 is a side view of the circumcision device shown in FIG. 1.

Referring to FIG. 2, central bridge portion 22 has transversely opposing sides. The pair of side bridge portions 24 transversely extend from respective sides of central bridge portion 22. FIG. 2 further illustrates that handle 28 is thinner, and thus structurally weaker, at and adjacent to junction 30 than any other portion of the handle to thereby make the handle readily breakable and detachable from central bridge portion 22 of bridge 20 at junction 30.

Figure 3:
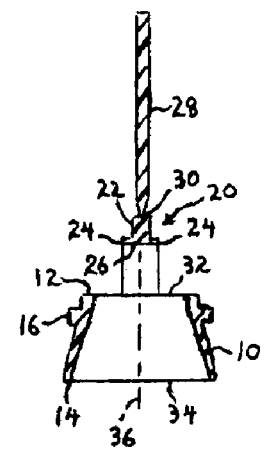
FIG. 3 is a cross-sectional view of the circumcision device as viewed along line 3-3 in FIG. 1.

Referring to FIG. 3, ring 10 is shown as having a tapered interior surface. Anterior end 12 is open, and an anterior opening 32 is defined by the interior surface at the anterior end. Posterior end 14 is also open, and a posterior opening 34 is defined by the interior surface at the posterior end which is larger than anterior opening 32. A longitudinal axis 36 extends between and through anterior opening 32 and posterior opening 34 so as to intersect bridge 20. It can be seen from FIG. 3 that side bridge portions 24 are substantially thinner than central bridge portion 22. Side bridge portions 24 thus serve to widen bridge 20 without significantly contributing to the weight or amount of required material for the circumcision device. A wider bridge 20 disperses the contact pressure upon a glans that comes into contact with inner surface 26, thereby minimizing any contact irritation or potential deformation of the glans.

FIG. 3 further shows bridge 20 extending over anterior opening 32. The distance between anterior opening 32 and inner surface 26 as measured along longitudinal axis 36 is preferably about ½-¾ the diameter of the anterior opening, and most preferably about ⅔ the diameter of the anterior opening. The preferred distance cited, and thus the maximum allowed protrusion of a glans from anterior end 12, provides a desirable compromise between little or no allowed protrusion and excessive protrusion. Although within the scope of broad aspects of the invention, allowing little or no protrusion can cause undue contact pressure upon the glans by the bridge and possibly damage the glans, and urine deflected by the bridge could become entrapped or collect within the ring and cause other problems. The preferred distance cited desirably allows some protrusion of the glans, but not to an extent that could cause the complications previously discussed. Finally with reference to FIG. 3, handle 28 is aligned with longitudinal axis 36 so as to extend longitudinally and outwardly from junction 30.

Figure 4:
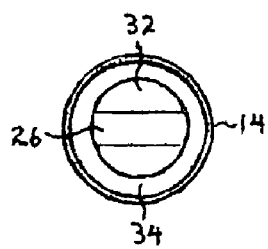
FIG. 4 is a posterior end view of the circumcision device.

Referring to FIG. 4, this posterior end view of the circumcision device shows the posterior end 14, posterior opening 34, anterior opening 32 as viewed through the posterior opening, and inner surface 26 of the bridge as extending over anterior opening 32. Posterior end 14, posterior opening 34, and anterior opening 32 are all preferably circular in shape as illustrated.

Figure 5:
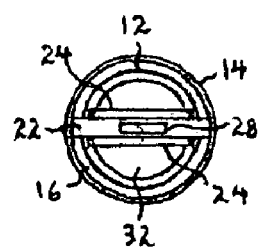
FIG. 5 is an anterior end view of the circumcision device.

Referring to FIG. 5, this anterior end view of the circumcision device shows anterior end 12, anterior opening 32, flange 16, the outer boundary of posterior end 14, central bridge portion 22, side bridge portions 24, and the anterior end of handle 28. Anterior end 12 is preferably circular in shape, and flange 16 is preferably annular in shape as illustrated.

The preferred material for the circumcision device is a hard, smooth, and substantially transparent plastic. To assist in preventing infections, the plastic can be coated or impregnated with an antibiotic.

In the circumcision of a penis, the foreskin is pulled open with clamps, and a probe is inserted to tear the foreskin off the glans. A "dorsal crush" is made to prevent bleeding, and a longitudinal slit is then cut in the foreskin. The foreskin is laid back to expose the glans. The surgeon grasps the handle of the circumcision device and positions the ring over the glans. The foreskin is pulled distally over the ring, followed by the tying of a ligature around the foreskin so as to compress the foreskin into the previously described groove. The ligature should have good tensile strength to avoid breakage, is preferably braided to avoid slipping or loosening when tying a knot, and can be coated or impregnated with an antibiotic to avoid infection. Excess foreskin distal to the ligature and adjacent to the anterior end of the ring is trimmed off with scissors or scalpel. Finally, the handle is broken off and detached from the bridge, leaving the bridge connected to the ring and flange. The circumcision device and penis at this point of the circumcision procedure is shown in FIG. 6.

Figure 6:
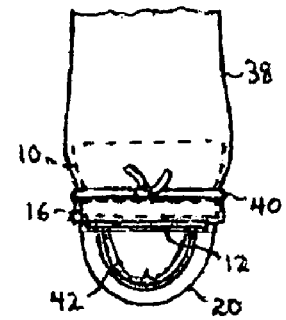
FIG. 6 is a view of the circumcision device with its handle detached from the bridge, being positioned and prepared for circumcision of a penis. The limitation of glans protrusion is further shown, as will be discussed further below.

FIG. 6 shows the foreskin 38 of the penis as received over ring 10 and its associated flange 16. Ring 10 and flange 16 are shown in broken lines. As discussed above, ligature 40 is received around foreskin 38 so as to compress the foreskin into groove 18 (see FIG. 1). Glans 42 partially protrudes from anterior end 12 so that its tip is in contact with the inner surface of bridge 20. Therefore, bridge 20 acts as an obstruction to glans 42 to thereby limit the protrusion thereof from anterior end 12. Protrusion is limited sufficiently so that after 3-8 days, ring 10 and attached bridge 20 are allowed to fall off the penis once foreskin 38 under and distal to ligature 40 dies. As noted previously, excessive protrusion of the glans may prevent the ring from falling off the penis as intended. Prevention of excessive protrusion by bridge 20 avoids other possible complications such as infection or damage to the urethra that result from constriction of the penis by the ring. In addition, selection of the proper ring size is less critical in view of the limitation of protrusion by bridge 20.

Obviously, many modifications and variations of the present invention are possible in light of the above teachings. For example, instead of fixedly connecting the bridge to the anterior end of the bridge at diametrically opposite points as in the illustrated embodiment, the bridge could trisect the anterior end to form a tripodal structure. Other alternative configurations of the bridge are within the scope of the invention as long as the bridge extends over the anterior opening, to thereby act as an obstruction to the glans, and is connected to the anterior end at circumferentially spaced points thereof. It is, therefore, to be understood that within the scope of the appended claims the invention can be practiced otherwise than as specifically described.

That which is claimed is:

1. A circumcision device comprising:
  a ring having a tapered interior surface, an open anterior end, an anterior opening defined by the interior surface at the anterior end, an open posterior end, a posterior opening defined by the interior surface at the posterior end which is larger than the anterior opening, a longitudinal axis extending between and through the anterior and posterior openings, an exterior surface, and a groove circumferentially defined around the exterior surface adjacent to the anterior end;
  a bridge extending over the anterior opening and fixedly connected to the anterior end at circumferentially spaced points thereof; and
  a handle fixedly but frangibly connected to the bridge at a junction between the handle and bridge, the handle extending longitudinally and outwardly from the junction and being structurally weaker at and adjacent to the junction than any other portion of the handle to thereby make the handle readily breakable and detachable from the bridge at the junction.

2. A circumcision device as recited in claim 1 wherein the anterior end and anterior opening are substantially circular in shape, and the posterior end and posterior opening are also substantially circular in shape.

3. A circumcision device as recited in claim 1 further comprising an exterior substantially annular flange integral with the ring, there being a junction of the flange with the ring which forms the groove.

4. A circumcision device as recited in claim 1 wherein the points of connection of the bridge to the anterior end are substantially diametrically opposite one another.

5. A circumcision device as recited in claim 4 wherein the bridge has an inner surface, extending between the points of connection to the anterior end, that is transversely arcuate in shape.

6. A circumcision device as recited in claim 5 wherein the longitudinal axis of the ring intersects the bridge.

7. A circumcision device as recited in claim 6 wherein the anterior opening has a diameter, and the distance between the anterior opening and inner surface of the bridge as measured along the longitudinal axis of the ring is about ½-¾ the diameter of the anterior opening.

8. A circumcision device as recited in claim 7 wherein said distance is about ⅔ the diameter of the anterior opening.

9. A circumcision device as recited in claim 7 wherein the bridge includes a central bridge portion, having transversely opposing sides, and a pair of side bridge portions that transversely extend from respective sides of the central bridge portion, the side bridge portions being thinner than the central bridge portion and defining with the central bridge portion the inner surface of the bridge.

10. A circumcision device as recited in claim 9 wherein the central bridge portion and side bridge portions are fixedly connected to the anterior end of the ring, and only the central bridge portion is fixedly connected to the flange.

11. A circumcision device as recited in claim 1 wherein the handle is thinner, and thereby structurally weaker, at and adjacent to the junction than any other portion of the handle.

* * * * *